United States Patent

Mewshaw et al.

[11] Patent Number: 5,872,144
[45] Date of Patent: Feb. 16, 1999

[54] 4-AMINOETHOXYINDAZOLE DERIVATIVES

[75] Inventors: Richard Eric Mewshaw, Princeton, N.J.; Anthonie Johan Verwijs, Felton, Del.

[73] Assignee: American Home Products Corporation, Madison, N.J.

[21] Appl. No.: 24,600

[22] Filed: Feb. 17, 1998

Related U.S. Application Data

[60] Provisional application No. 60/038,684 Frb. 18, 1997.
[51] Int. Cl.[6] .................... A61K 31/415; C07D 409/12; C07D 231/56
[52] U.S. Cl. ........................ 514/403; 548/362.5
[58] Field of Search ................ 548/362.5; 514/403

[56] References Cited

FOREIGN PATENT DOCUMENTS

WO9421626 9/1994 WIPO .
WO9421630 9/1994 WIPO .
9500509 5/1995 WIPO .

OTHER PUBLICATIONS

Chem. Abs., vol. 117, No. 23; 225909n (Dec. 1992).
Chem. Abs., vol. 114, No. 3; 23858x (Jan. 1991).

*Primary Examiner*—Patricia L. Morris
*Attorney, Agent, or Firm*—Rebecca R. Barrett

[57] ABSTRACT

This invention relates to dopamine $D_2$ agonists of the formula

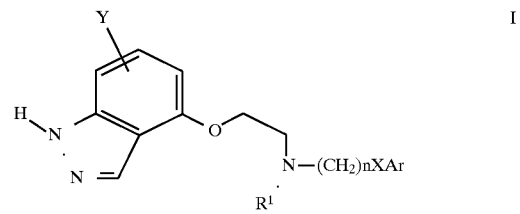

wherein:

Y is hydrogen, halogen, or $C_1$–$C_6$ alkoxy;

$R^1$ is hydrogen or $C_1$–$C_6$ alkyl;

X is methylene, oxygen or carbonyl;

Ar is phenyl or thienyl, each optionally substituted with 1–2 groups independently selected from $C_1$–$C_6$ alkoxy, $C_1$–$C_6$ alkyl, halogen, trifluoromethyl and phenyl;

n=1–4, or pharmaceutically acceptable salts thereof. Dopamine $D_2$ agonists are useful in the treatment of schizophrenia, Tourette's syndrome, drug and alcohol addiction, and also useful in the treatment of Parkinson's disease.

5 Claims, No Drawings

4-AMINOETHOXYINDAZOLE DERIVATIVES

This application claims benefit of priority to provisional patent application number 60/038,684 filed Feb. 18, 1997.

FIELD OF INVENTION

This invention relates to 4-aminoethoxyindazole derivatives having dopamine $D_2$ agonist activity useful for antipsychotic effects and antiparkinsonism.

BACKGROUND OF INVENTION

Efforts to induce antipsychotic activity with dopamine autoreceptor agonists have been successful (Dorsini et al., Adv. Biochem. Psychopharmacol, 16, 645–648, 1977; Tamminga et al., Science, 200, 567–568, 1975; and Tamminga et al., Psychiatry, 398–402, 1986). A method for determining intrinsic activity at the dopamine $D_2$ receptor was recently reported [Lahti et al., Mol. Pharm., 42, 432–438, (1993)]. Intrinsic activity is predicted using the ratio of the "low-affinity agonist" (LowAg) state of the receptor and the "high-affinity agonist" (HighAg) state of the receptor, i.e. LowAg/HighAg. These ratios correlate with the agonist, partial agonist, and antagonist activities of a given compound, which activities characterize a compounds ability to elicit an antipsychotic effect. The compounds of this invention are dopamine agonists various degrees of intrinsic activity some of which are selective autoreceptor agonists, and therefore partial agonist (i.e. activate only autoreceptors versus postsynaptic $D_2$ dopamine receptors). As such, they provide functional modulation of the dopamine systems of the brain without the excessive blockade of the postsynaptic dopamine receptors which have been observed to be responsible for the serious side effects frequently exhibited by agents found otherwise clinically effective for the treatment of schizophrenia. Activation of the dopamine autoreceptors results in reduced neuronal firing a well as inhibition of dopamine synthesis and release and therefore provide a means of controlling hyperactivity of the dopaminergic systems. The compounds of this invention were also found to have high intrinsic activity and therefore they can behave as the natural neurotransmitter i.e. as full agonists. As such, they are useful in the treatment of diseases having abnormal concentrations of dopamine could be used as dopamine surrogates possibly in the treatment of Parkinson's disease. Additionally, the compounds of this invention are essentially free from extrapyramidal side effects (EPS).

SUMMARY OF THE INVENTION

The compounds of this invention are 4-aminoethoxy-benzimidazole derivatives which are illustrated by Formula I below

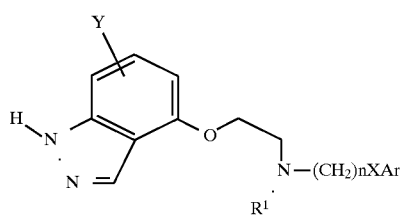

wherein:
Y is hydrogen, halogen, or $C_1$–$C_6$ alkoxy;
$R^1$ is hydrogen or $C_1$–$C_6$ alkyl;
X is methylene, oxygen or carbonyl;
Ar is phenyl or thienyl, each optionally substituted with 1–2 groups independently selected from $C_1$–$C_6$ alkoxy, $C_1$–$C_6$ alkyl, halogen, trifluoromethyl and phenyl;

n=1–4.

The compounds of this Formula I also may be used in the form of a pharmaceutically acceptable acid addition salt having the utility of the free base. Such salts, prepared by methods well known to the art are formed with both inorganic or organic acids, for example: fumaric, maleic, benzoic, ascorbic, pamoic, succinic, bismethylenesalicylic, methanesulfonic, ethanedisulfonic, acetic, oxalic, propionic, tartaric, salicyclic, citric, gluconic, lactic, malic, mandelic, cinnamic, citraconic, aspartic, stearic, palmitic, itaconic, glycolic, p-aminobenzoic, glutamic, benzene-sulfonic, hydrochloric hydrobromic, sulfuric, cyclohexylsulfamic, phosphoric and nitric acids.

The compounds of Formula I are generally prepared by the overall sequence indicated in Scheme I as follows:

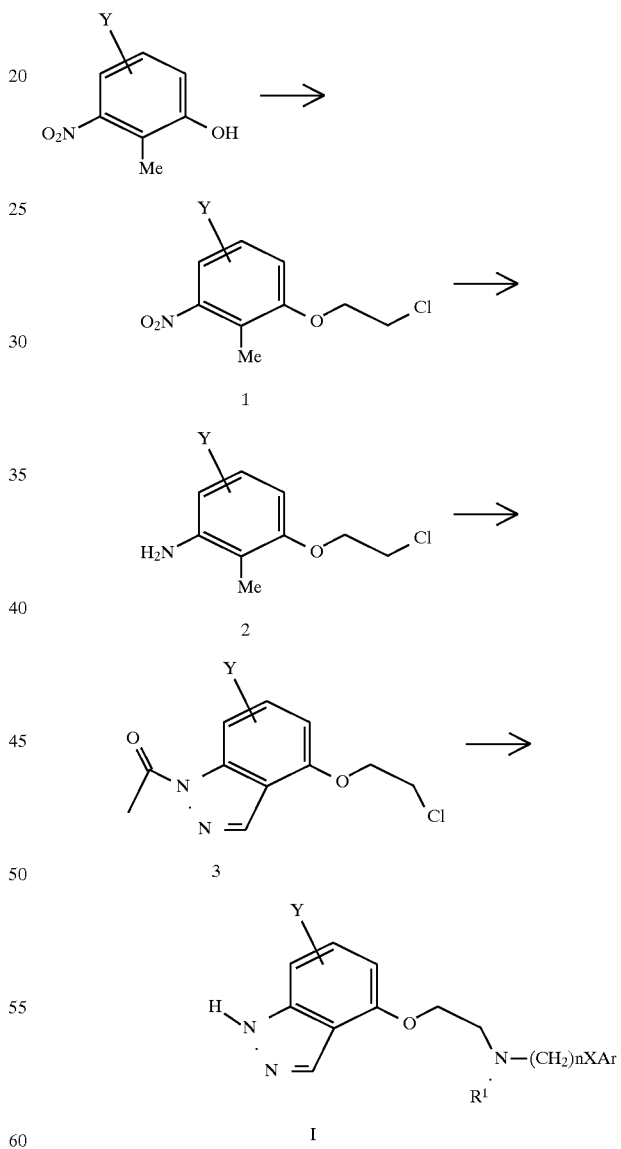

The following examples for preparation of intermediates and invention compounds are included for illustrative purposes and are not to be construed as limiting to this disclosure in any way. Those skilled in the art of organic synthesis may be aware of still other synthetic route to the invention compounds. The reagents and intermediates used herein are either commercially available or prepared according to standard literature procedures.

Intermediate 1

1-(2-Chloroethoxy)-2-methyl-3-nitrobenzene

To a solution of 2-methyl-3-nitro-phenol (3.0 g, 19.6 mmol), triphenylphosphine (7.2 g, 27.4 mmol), and chloroethanol (1.89 g, 23.5 mmol) in anhydrous tetrahydrofuran (70 mL) was slowly added a solution of diethylazidodicarboxylate (4.78 g, 27.4 mmol). After 1 h the reaction was complete and the solvent was removed and the residue dissolved in 1:1 ethyl acetate-hexanes (150 mL). After 30 min the solid triphenylphosphine oxide was filtered and the solvent again removed. The crude product was purified by chromatography (20% ethyl acetate-hexanes) to afford 4.2 g (100%) of a light yellow solid: mp 58°–59° C.

Elemental analysis for $C_9H_{10}ClNO_3$ Calc'd: C, 50.13; H, 4.68; N, 6.50 Found: C, 50.15; H, 4.66; N, 6.47

Intermediate 2

1-(2-Chloroethoxy)-2-methyl-3-aminobenzene

A mixture of 1-(2-chloroethoxy)-2-methyl-3-nitrobenzene (10.7 g, 50 mmol) in ethanol (200 mL) containing 500 mg of 5% palladium on carbon was hydrogenated at 50 psi for 4 h. The catalyst was filter through Solka Floc and the solvent removed under vacuum to afford 9.1 g (98.8%) a yellow oil: $^1$H NMR (CDCl$_3$) δ 2.76 (3H, s), 3.92 (2H, t, J=5.9 Hz), 4.40 (2H, t, J=5.9 Hz), 6.70 (1H, d, J=), 7.46 (1H, app t, J=), 8.04 (1H, d, J=), 8.24 (1H, s).

Intermediate 3

1-Acetyl-4-(2-chloroethoxy)-indazole

To a mixture of 1-(2-chloroethoxy)-2-methyl-3-aminobenzene (9.0 g, 48.6 mmol), acetic anhydride (15.4 mL, 163 mmol), and potassium acetate (5.0 g, 51 mmol)) at 80° C. was added dropwise isoamyl nitrite (10 mL, 75 mmol)). The reaction was stirred for 18 h at 80° C. then cooled to room temperature and filtered. The solvent was concentrated whereupon a solid is formed which is filtered and washed with hexanes to afford 9.3 g, (79.5%) of a yellow solid: mp 77°–79° C.; IR (KBr) 1710 cm-1; MS EI m/e 238/240 (M+); $^1$H NMR (CDCl$_3$) δ 2.79 (3H, s), 3.91 (2H, t, J=5.9 Hz), 4.41 (2H, t, J=5.9 Hz), 6.69 (1H, d, J=8 Hz), 7.44 (1H, app t, J=8 Hz), 8.03 (1H, d, J=8 Hz), 8.23 (1H, d, J=1 Hz).

Elemental analysis for $C_{11}H_{11}ClN_2O_3$ Calc'd: C, 55.36; H, 4.65; N, 11.74 Found: C, 55.17; H, 4.52; N, 11.40

EXAMPLE 1

Benzyl-[2-(1H-indazo-4-yloxy)-ethyl]-amine

A solution of 1-acetyl-4-(2-chloroethoxy)-indazole (1.0 g, 4.2 mmol) and benzylamine (1.8 g, 16.8 mmol) in anhydrous dimethylsulfoxide (10 mL) was heated to 100° C. for 18 h. The reaction was diluted with ether (100 mL) and washed with 10% aqueous sodium carbonate, brine, and dried over anhydrous magnesium sulfate, filtered and the solvent removed. Purification with chromatography (3% methanol-methylene chloride) afforded 600 mg (53%) of a yellow solid: mp 107°–108° C. The oxalate salt was prepared in ethanol as a white solid: mp 220°–221° C.

Elemental analysis for $C_{16}H_{17}N_3O.C_2H_2O_4$ Calc'd: C, 60.50 H, 5.36; N, 11.76 Found: C, 60.23 ; H, 5.23 N, 11.62

EXAMPLE 2

[2-(1H-Indazol-4-yloxy)-ethyl]-thiophen-2-ylmethyl-amine

Following the general procedure of Example 1 and substituting 2-thiophenemethylamine for benzylamine gave the tide compound in 87% yield. The compound was isolated as the oxalate salt from ethanol, mp 220°–221° C. (dec.).

Elemental analysis for $C_{14}H_{15}N_3OS.C_2H_2O_4$ Calc'd: C, 52.84 H, 4.71; N, 11.55 Found: C, 52.72; H, 4.61 N, 11.55

EXAMPLE 3

[2-(1H-Indazol-4-yloxy)-ethyl]-thiophen-3-ylmethyl-amine

Following the general procedure of Example 1 and substituting 2-thiophenemethylamine for benzylamine gave the title compound in 87% yield. The compound was isolated as the oxalate salt from ethanol, mp 215°–216° C.

Elemental analysis for $C_{14}H_{15}N_3OS.C_2H_2O_4$ Calc'd: C, 52.84 H, 4.71; N, 11.55 Found: C, 52.72 ; H, 4.61 N, 11.37

Pharmacology

The compounds of this invention are dopamine autoreceptor agonists, that is, they serve to modulate the synthesis and release of the neurotransmitter dopamine. They are thus useful for treatment of disorders of the dopaminergic system, such as schizophrenia, Parkinson's disease and Tourette's syndrome. Such agents are partial agonists at the postsynaptic dopamine $D_2$ receptor and are thereby useful in the treatment of alcohol and drug addiction.

Affinity for the dopamine autoreceptor was established by a modification of the standard experimental test procedure of Seemen and Schaus, *European Journal of Pharmacology* 203, 105–109, 1991, wherein homogenized rat striatal brain tissue is incubated with $^3$H-quinpirole (Quin.) and various concentrations of test compound, filtered and washed and counted in a Betaplate scintillation counter.

High affinity for the dopamine D-2 receptor was established by the standard experimental test procedure of Fields, et al., *Brain Res.,* 136, 578 (1977) and Yamamura et al., eds., *Neurotransmitter Receptor Binding,* Raven Press, N.Y. (1978) wherein homogenized limbic brain tissue is incubated with $^3$H-spiroperidol (Spiper.) and various concentrations of test compound, filtered and washed and shaken with Hydrofluor scintillation cocktail (National Diagnostics) and counted in a Packard 460 CD scintillation counter.

The results of the tests with compounds representative of this invention are given below.

| Example No. | IC$_{50}$ (nM) D$_2$ Quin. | IC$_{50}$ (nM) D$_2$ Spiper | Ratio |
| --- | --- | --- | --- |
| 1 | 2.23 | 333 | 151 |
| 2 | 4.30 | 1092 | 254 |
| 3 | 2.78 | — | — |

Hence, the compounds of this invention effect the synthesis of the neurotransmitter dopamine and thus are useful in the treatment of dopaminergic disorders such as schizophrenia, Parkinson's disease, Tourette's Syndrome, alcohol addiction, cocaine addiction, and addiction to analogous drugs.

Pharmaceutical Composition

Applicable solid carriers for pharmaceutical compositions containing the compounds of this invention can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific psychosis must be subjectively determined by the attending physician. The variables involved include the specific psychosis and the size, age and response pattern of the patient.

What is claimed is:

1. A compound having the formula

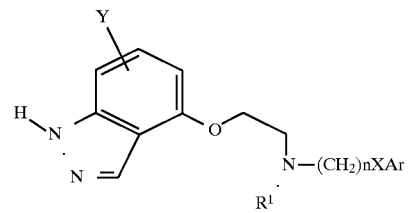

wherein:

Y is hydrogen, halogen, or $C_1$–$C_6$ alkoxy;

$R^1$ is hydrogen or $C_1$–$C_6$ alkyl;

X is methylene, oxygen or carbonyl;

Ar is phenyl or thienyl, each optionally substituted with 1–2 groups independently selected from $C_1$–$C_6$ alkoxy, $C_1$–$C_6$ alkyl, halogen, trifluoromethyl and phenyl;

n=1–4, or a pharmaceutically acceptable salt thereof.

2. A compound according to claim 1 which is benzyl-[2-(1H-indazo-4-yloxy)-ethyl]-amine or a pharmaceutically acceptable salt thereof.

3. A compound according to claim 1 which is [2-(1H-indazol-4-yloxy)-ethyl]-thiophen-2-ylmethyl-amine or a pharmaceutically acceptable salt thereof.

4. A compound according to claim 1 which is [2-(1H-indazol-4yloxy)-ethyl]-thiophen-3-ylmethyl-amine or a pharmaceutically acceptable salt thereof.

5. A pharmaceutical composition comprising a pharmaceutically acceptable carrier and a therapeutically effective amount of a compound of the formula

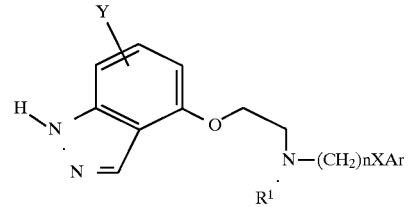

wherein:

Y is hydrogen, halogen, or $C_1$–$C_6$ alkoxy;

$R^1$ is hydrogen or $C_1$–$C_6$ alkyl;

X is methylene, oxygen or carbonyl;

Ar is phenyl or thienyl, each optionally substituted with 1–2 groups independently selected from $C_1$–$C_6$ alkoxy, $C_1$–$C_6$ alkyl, halogen, trifluoromethyl and phenyl;

n=1–4, or a pharmaceutically acceptable salt thereof.

* * * * *